US010655166B2

(12) United States Patent
Su et al.

(10) Patent No.: US 10,655,166 B2
(45) Date of Patent: May 19, 2020

(54) ELECTRICALLY ACTIVE COMBINATORIAL CHEMICAL (EACC) CHIP FOR BIOCHEMICAL ANALYTE DETECTION

(71) Applicant: Intel Corporation, Santa Clara, CA (US)

(72) Inventors: Xing Su, Cupertino, CA (US); Lei B. Sun, Santa Clara, CA (US); Jacque H. Georger, Jr., Holden, MA (US)

(73) Assignee: Intel Corporation, Santa Clara, CA (US)

( * ) Notice: Subject to any disclaimer, the term of this patent is extended or adjusted under 35 U.S.C. 154(b) by 236 days.

(21) Appl. No.: 15/727,296

(22) Filed: Oct. 6, 2017

(65) Prior Publication Data

US 2018/0187249 A1  Jul. 5, 2018

Related U.S. Application Data

(60) Continuation of application No. 12/964,814, filed on Dec. 10, 2010, now abandoned, which is a division of application No. 11/025,502, filed on Dec. 28, 2004, now Pat. No. 7,879,764.

(51) Int. Cl.
| | |
|---|---|
| *C12Q 1/6837* | (2018.01) |
| *B01J 19/00* | (2006.01) |
| *B01L 3/00* | (2006.01) |
| *B82Y 15/00* | (2011.01) |
| *B82Y 30/00* | (2011.01) |
| *G01N 33/543* | (2006.01) |
| *C40B 60/04* | (2006.01) |

(52) U.S. Cl.
CPC ........ *C12Q 1/6837* (2013.01); *B01J 19/0046* (2013.01); *B01L 3/5085* (2013.01); *B82Y 15/00* (2013.01); *B82Y 30/00* (2013.01); *G01N 33/5438* (2013.01); *B01J 2219/0061* (2013.01); *B01J 2219/0063* (2013.01); *B01J 2219/00317* (2013.01); *B01J 2219/00527* (2013.01); *B01J 2219/00596* (2013.01); *B01J 2219/00608* (2013.01); *B01J 2219/00612* (2013.01); *B01J 2219/00621* (2013.01); *B01J 2219/00626* (2013.01); *B01J 2219/00628* (2013.01); *B01J 2219/00637* (2013.01); *B01J 2219/00653* (2013.01); *B01J 2219/00659* (2013.01); *B01J 2219/00662* (2013.01); *B01J 2219/00704* (2013.01); *B01J 2219/00722* (2013.01); *B01L 2300/0636* (2013.01); *B01L 2300/0819* (2013.01); *C40B 60/04* (2013.01)

(58) Field of Classification Search
None
See application file for complete search history.

(56) References Cited

U.S. PATENT DOCUMENTS

| | | | |
|---|---|---|---|
| 5,077,085 A | 12/1991 | Schnur et al. | |
| 5,079,600 A | 1/1992 | Schnur et al. | |
| 5,510,628 A | 4/1996 | Georger, Jr. et al. | |
| 6,340,568 B2 | 1/2002 | Hefti | |
| 6,514,767 B1 | 2/2003 | Natan | |
| 6,566,079 B2 * | 5/2003 | Hefti ...................... | H01J 49/04 435/287.1 |
| 6,649,403 B1 | 11/2003 | Mcdevitt et al. | |
| 6,952,651 B2 | 10/2005 | Su | |
| 7,879,764 B2 | 2/2011 | Su et al. | |
| 2002/0095073 A1 | 7/2002 | Jacobs et al. | |
| 2002/0187509 A1 | 12/2002 | Shao et al. | |
| 2003/0096232 A1* | 5/2003 | Kris et al. ............ | C12Q 1/6816 435/6.11 |
| 2003/0113713 A1 | 6/2003 | Glezer et al. | |
| 2003/0203405 A1* | 10/2003 | Carlson ................ | B01J 19/0046 506/15 |
| 2004/0081967 A1 | 4/2004 | Leproust et al. | |
| 2004/0235051 A1 | 11/2004 | Carlson | |
| 2004/0253642 A1* | 12/2004 | Zimmermann et al. ...... | C40B 20/04 506/7 |
| 2005/0170385 A1* | 8/2005 | Carlson ................ | C12Q 1/6804 435/6.14 |
| 2011/0136693 A1 | 6/2011 | Su et al. | |

FOREIGN PATENT DOCUMENTS

| | | | |
|---|---|---|---|
| DE | 112005003134 B4 | 3/2018 | |
| EP | 1502102 A2 | 2/2005 | |
| EP | 1573066 A1 | 9/2005 | |
| WO | WO-9810289 A1 | 3/1998 | |
| WO | WO-02084285 A2 * | 10/2002 | ............. B82Y 30/00 |
| WO | WO-02084285 A2 | 10/2002 | |
| WO | WO-03077851 A2 | 9/2003 | |
| WO | WO-2004053165 A1 | 6/2004 | |
| WO | WO-2006071946 | 7/2006 | |

OTHER PUBLICATIONS

Joos et al., "Covalent Attachment of Hybridizable Oligonucleotides to Glass Supports," Anal. Biochem. 1997, 247:96-101. (Year: 1997).*

(Continued)

*Primary Examiner* — Kaijiang Zhang
(74) *Attorney, Agent, or Firm* — Schwegman Lundberg & Woessner, P.A.

(57) ABSTRACT

Apparatus and methods are disclosed for electrically active combinatorial-chemical (EACC) chips for biochemical analyte detection. An apparatus includes a substrate that has an array of regions defining multiple cells, wherein each of the cells includes a reaction cavity that contains multiple functional binding groups. A method of detecting an analyte providing the reaction cavity between a source and a drain or a pair of electrodes, applying a voltage and monitoring a parameter indicative of an analyte characteristic. A process of fabricating an EACC include bonding an analyte to the multiple functional binding groups of each reaction cavity, and forming an analyte sensing structure including the substrate.

17 Claims, 12 Drawing Sheets

(56) References Cited

OTHER PUBLICATIONS

"U.S. Appl. No. 11/025,502, Advisory Action dated Mar. 31, 2009", 6 pgs.
"U.S. Appl. No. 11/025,502, Applicant's Summary of Examiner Interview filed Oct. 19, 2007", 2 pgs.
"U.S. Appl. No. 11/025,502, Examiner Interview Summary dated Sep. 20, 2007", 3 pgs.
"U.S. Appl. No. 11/025,502, Final Office Action dated Jun. 3, 2010", 18 pgs.
"U.S. Appl. No. 11/025,502, Final Office Action dated Nov. 4, 2008", 12 pgs.
"U.S. Appl. No. 11/025,502, Final Office Action dated Nov. 7, 2007", 10 pgs.
"U.S. Appl. No. 11/025,502, Non Final Office Action dated Apr. 28, 2008", 10 pgs.
"U.S. Appl. No. 11/025,502, Non Final Office Action dated Jun. 5, 2007", 13 pgs.
"U.S. Appl. No. 11/025,502, Non Final Office Action dated Jun. 17, 2009", 16 pgs.
"U.S. Appl. No. 11/025,502, Notice of Allowance dated Sep. 10, 2010", 4 pgs.
"U.S. Appl. No. 11/025,502, Notice of Allowance dated Sep. 28, 2010", 2 pgs.
"U.S. Appl. No. 11/025,502, Notice of Non-Compliant Amendment dated Jul. 28, 2010", 4 pgs.
"U.S. Appl. No. 11/025,502, Preliminary Amendment filed Mar. 24, 2005", 3 pgs.
"U.S. Appl. No. 11/025,502, Response filed Feb. 6, 2008 to Final Office Action dated Nov. 7, 2007", 12 pgs.
"U.S. Appl. No. 11/025,502, Response filed Mar. 4, 2009 to Final Office Action dated Nov. 4, 2008", 9 pgs.
"U.S. Appl. No. 11/025,502, Response filed Mar. 6, 2007 to Restriction Requirement dated Feb. 27, 2007", 2 pgs.
"U.S. Appl. No. 11/025,502, Response filed Mar. 23, 2010 to Restriction Requirement dated Feb. 24, 2010", 1 pg.
"U.S. Appl. No. 11/025,502, Response filed Jul. 15, 2010 to Final Office Action dated Jun. 3, 2010", 9 pgs.
"U.S. Appl. No. 11/025,502, Response filed Jul. 28, 2008 to Non Final Office Action dated Apr. 28, 2008", 7 pgs.
"U.S. Appl. No. 11/025,502, Response filed Aug. 30, 2010 to Notice of Non-Compliant Amendment dated Jul. 28, 2010", 9 pgs.
"U.S. Appl. No. 11/025,502, Response filed Sep. 13, 2007 to Non Final Office Action dated Jun. 5, 2007", 15 pgs.
"U.S. Appl. No. 11/025,502, Response filed Oct. 19, 2009 to Non Final Office Action dated Jun. 17, 2009", 11 pgs.
"U.S. Appl. No. 11/025,502, Restriction Requirement dated Feb. 24, 2010", 5 pgs.
"U.S. Appl. No. 11/025,502, Restriction Requirement dated Feb. 27, 2007", 9 pgs.
"German Application Serial No. 112005003134.9, Office Action dated Aug. 11, 2017", (English Translation), 4 pgs.
"German Application Serial No. 112005003134.9, Response filed Oct. 24, 2017 to Office Action dated Aug. 11, 2017", w/ claims in English, 72 pgs.
"U.S. Appl. No. 12/964,814, Advisory Action dated Dec. 29, 2014", 3 pgs.
"U.S. Appl. No. 12/964,814, Final Office Action dated Apr. 6, 2017", 43 pgs.
"U.S. Appl. No. 12/964,814, Final Office Action dated Sep. 18, 2014", 34 pgs.
"U.S. Appl. No. 12/964,814, Final Office Action dated Sep. 19, 2016", 40 pgs.
"U.S. Appl. No. 12/964,814, Non Final Office Action dated Jan. 29, 2016", 49 pgs.
"U.S. Appl. No. 12/964,814, Non Final Office Action dated Apr. 10, 2014", 31 pgs.
"U.S. Appl. No. 12/964,814, Non Final Office Action dated Apr. 10, 2017", 31 pgs.
"U.S. Appl. No. 12/964,814, Preliminary Amendment filed Dec. 10, 2010", 38 pgs.
"U.S. Appl. No. 12/964,814, Response filed Jan. 13, 2014 to Restriction Requirement dated Dec. 13, 2013", 2 pgs.
"U.S. Appl. No. 12/964,814, Response filed Jan. 16, 2015 to Advisory Action dated Dec. 29, 2014", 11 pgs.
"U.S. Appl. No. 12/964,814, Response filed May 31, 2016 to Non Final Office Action dated Jan. 29, 2016", 9 pgs.
"U.S. Appl. No. 12/964,814, Response filed Jul. 10, 2014 to Non Final Office Action dated Apr. 10, 2014", 10 pgs.
"U.S. Appl. No. 12/964,814, Response filed Nov. 30, 2016 to Final Office Action dated Sep. 19, 2016", 10 pgs.
"U.S. Appl. No. 12/964,814, Response filed Dec. 18, 2014 to Final Office Action dated Sep. 18, 2014", 11 pgs.
"U.S. Appl. No. 12/964,814, Restriction Requirement dated Dec. 13, 2013", 8 pgs.
"U.S. Appl. No. 12/964,814, Supplemental Preliminary Amendment filed Feb. 4, 2011", 4 pgs.
"U.S. Appl. No. 12/964,814, Supplemental Preliminary Amendment filed Feb. 23, 2011", 47 pgs.
"British Application Serial No. 0714458.7, Search and Examination Report dated Jun. 15, 2009".
"German Application Serial No. 112005003134.9, Office Action dated Mar. 18, 2013", 6 pgs.
"Japanese Application Serial No. 2007-548596, Office Action dated Jun. 22, 2010".
"Pharmacomer Technology Platform", Surface Logix, Inc.—Drug Development Platform, [Online] Retrieved from the Internet : <www.surfacelogix.com>, (Dec. 22, 2004).
Alexandar, Star, et al., "Electronic Detection of Specific Protein Binding Using Nanotube FET Devices", American Chemical Society, Nano Letters, vol. 3, No. 4, (2003), 459-463.
Janes, et al., "Self-assembled Metal/Molecules/Semiconductor Nanostructures for Electronic Device and Contact Applications", Journal of Electronic Materials 29(5), (2000), 6 pgs.
Joos, et al., "Covalent Attachment of Hybridizable Oligonucleotides to Glass Supports", Anal. Biochem, 247, (1997), 96-101.
Robert, J Chen, et al., "Noncovalent functionalization of carbon nanotubes for highly specific electronic biosensors", PNAS, vol. 100, (Apr. 29, 2003), 4984-4989.
Shawn, P Mulvaney, et al., "Glass-Coated, Analyte-Tagged Nanoparticles: A New Tagging System Based on Detection with Surface-Enhanced Raman Scattering", Langmuir, vol. 19, (2003), 4784-4790.
William, E Doering, et al., "Spectroscopic Tags Using Dye-Embedded Nanoparticles and Surface-Enhanced Raman Scattering", Analytical Chemistry, 6171-6176.
Yakimov, et al., "Long-range Coulomb interaction in arrays of self-assembled quantum dots", Physical Review B, 61(16), (2000), 10868-10876.

* cited by examiner

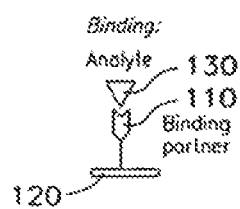
FIG. 1A
PRIOR ART
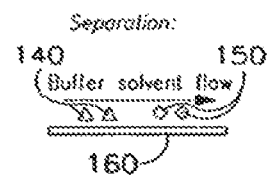
FIG. 1B
PRIOR ART
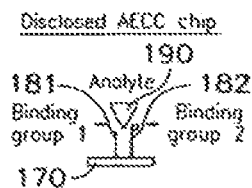
FIG. 1C
FIG. 2A
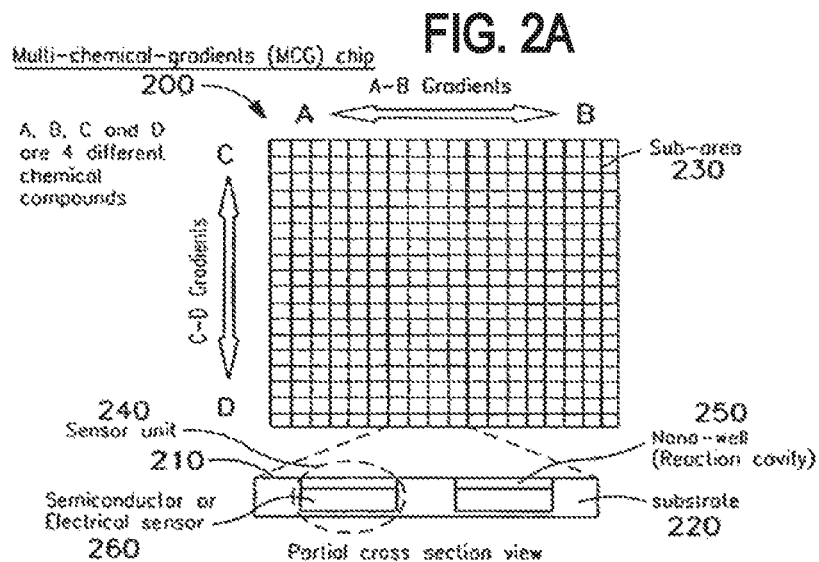
FIG. 2B

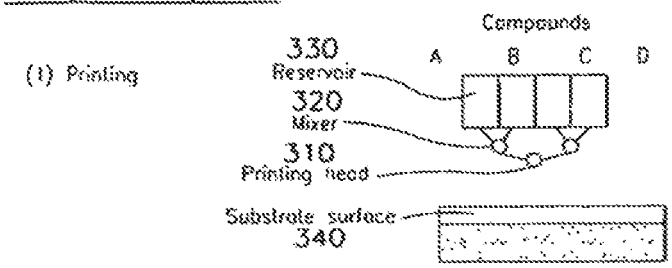
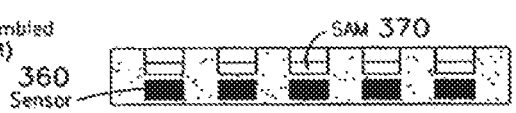
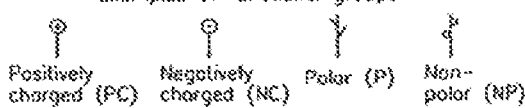
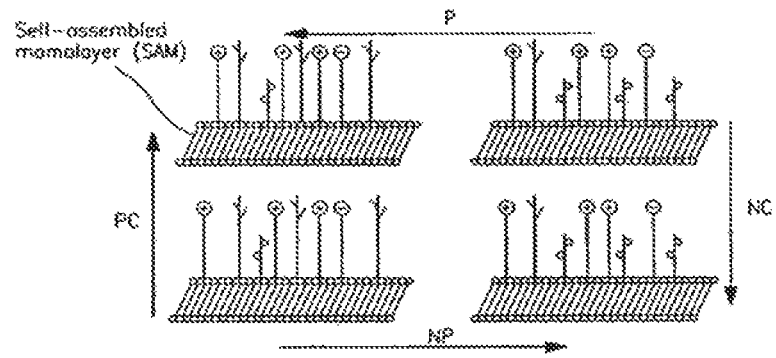
FIG. 4 multiple MCG areas that are different in
other variables:

1. Molecular chain length
2. Position of functional groups in a molecule
3. Distance between functional groups
4. Number of functional groups per molecule
5. Ratio of mixed functional groups per molecule
6. Arrangement of mixed functional groups in a molecule
7. Total density of functional group on a surface

| MCG area 1 | MCG area 2 |
|---|---|
| MCG area 3 | MCG area 4 |

FIG. 5

Examples of sensors

1) For field effect measurement

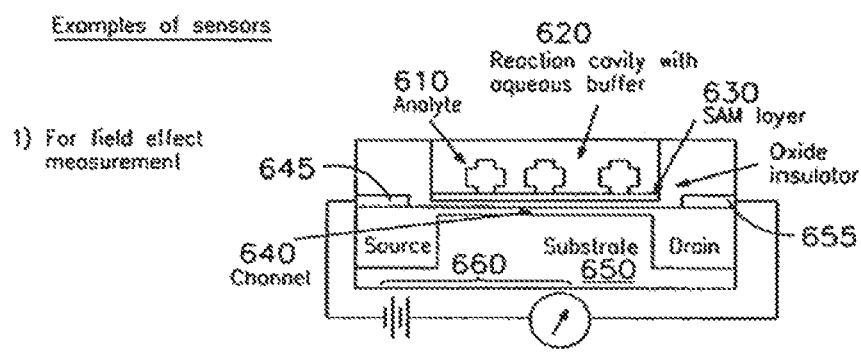

FIG. 6A

2) For capacitance or impedance measurement

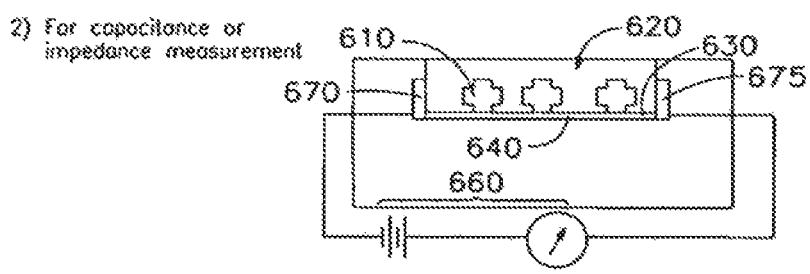

FIG. 6B

(+) Charged molecule (-) Charged molecule

Halogenated molecule

Hydrophobic molecule

ELECTRICALLY ACTIVE COMBINATORIAL CHEMICAL (EACC) CHIP FOR BIOCHEMICAL ANALYTE DETECTION

BACKGROUND OF THE INVENTION

Field of the Invention

Embodiments of the invention relate generally to the field of biological and/or chemical sensing. More particularly, embodiments of the invention relate to electrically active combinatorial-chemical (EACC) chips for biochemical analyte detection.

Background Information

Currently, biological and chemical analyte detections are based primarily on specific interaction between analytes and their binding partners. To perform high throughput assays, a large number of molecular probes need to be immobilized on a surface to form a microarray. Such microarrays are sometimes referred to as bio-chips (e.g., protein chips or gene chips). Preparing a large number of specific polymeric probes (e.g., antibodies or nucleic acids) is, however, both time-consuming and costly. Moreover, immobilizing the polymeric probes in discrete small surface areas is technically difficult and expensive. It is desired to have a more efficient approach to preparing and immobilizing probes.

Traditional approaches to making biochips involve chemically preparing polymeric probes and then subsequently spotting the chemically prepared polymeric probes on the chips. However, the minimum feature size attainable with these probes is typically >100 um for a protein chip (array), or >1 um for a gene chip (array). It is desired to have smaller feature sizes available in the future. While higher density bio-chips are clearly desirable from the perspective of both cost to manufacture and clinical efficiency, fabricating higher density bio-chips based on smaller polymeric probe feature sizes is both technically challenging and time-consuming. It is desired to have an approach that will permit the fabrication of chips based on smaller probe feature sizes.

Referring to FIGS. 1A and 1B, current biochips for direct analyte detection (antibody chips, DNA chips, aptamer chips) are based on interactions of analytes with their polymeric binding partners (probes), each of the latter of which presents unique intra molecular binding sites. Referring to FIG. 1A, a binding partner (probe) 110 is immobilized on a substrate 120. The binding partner 110 then binds with an analyte 130, thereby enabling the detection of the analyte 130. This binding approach is based on the principle of using a single, unique and large molecule for specific binding of analytes. This approach is highly specific and accurate, and generally involves small dimension(s). On the other hand, this approach is very costly and time-consuming because of the need to obtain analyte-specific probes or binding partners, and is generally inflexible. Also, as only known probes are used to detect known analytes; but not-yet-identified analytes are undetectable. It is desired, therefore, to have an approach that can detect unknown analytes.

Referring to FIG. 1B, two different types of analytes 140, 150 are dispersed across a substrate 160 by a buffer solvent flow. The analytes 140, 150 are spatially segregated across a surface of the substrate 160, thereby enabling separation of two different analytes 140, 150. The resulting spatial segregation permits detection of individual analytes. Separation in this instance is based on the principle of buffer solvent flow. This approach is low cost, fast, and flexible, but is less specific and less accurate than is desired, and it involves large dimension(s). Another technique might involve molecular migration in a gel (electrophoresis) based on size and molecular weight.

Protein binding to a surface may be affected by the chemical property of the surface. In this way, protein chips with different binding surfaces have been produced. Chromagraphic and spectrographic binding surface technologies have also been evolving, wherein bio-chip detections are typically read by optical methods. When the chip feature (spot) size becomes <1 um, however, optical detection becomes impractical. It is desired to have an approach that enables detection and reading with higher density bio-chips.

Electronic sensors for biomolecule detection have also been demonstrated. Although such electronic sensors have the potential to overcome the spatial limitations of optical detection, electronic sensors by themselves do not appear to obviate the underlying feature size limitations of the polymeric probe-analyte paradigm.

Self aligned monolayers have been demonstrated. The formation of patterned co-planar monolayers (which can be termed ultra thin films) and the use of those patterns to selectively bind colloidal catalysts & plate electroless metals selectively at high resolution are under investigation. Further research into the formation of ultra thin films for the selective adhesion of various types of biological cells is ongoing.

Heretofore, the requirements of a more efficient approach to preparing and immobilizing probes, smaller probe feature sizes, the ability to detect unknown analytes and the detection and reading of higher density bio-chips have not been fully met. It is therefore desired provide techniques that meet these goals.

DETAILED DESCRIPTION OF THE PREFERRED EMBODIMENTS OF THE INVENTION

The drawings accompanying and forming part of this specification are included to depict certain aspects of embodiments of the invention. A clearer conception of the embodiments of the invention, and of the components and operation of systems provided with embodiments of the invention, will become more readily apparent by referring to the exemplary, and therefore nonlimiting, embodiments illustrated in the drawings, wherein identical reference numerals designate the same elements. The embodiments of the invention may be better understood by reference to one or more of these drawings in combination with the description presented herein. It should be noted that the features illustrated in the drawings are not necessarily drawn to scale. Brief descriptions are provided below, followed a detailed description of the preferred embodiments in view of the illustrative drawings.

FIGS. 1A and 1B illustrate conventional techniques for binding and separating analytes.

FIG. 1C illustrates the use of a plurality of different binding groups to detect an analyte, representing an embodiment of the invention.

FIGS. 2A and 2B illustrate top plan and partial cross section views, respectively, of a combinatorial-chemical chip, representing an embodiment of the invention.

FIGS. 3A-3C illustrate a combinatorial printing head, a side view of filled reaction cavities and a side view of mixed self assembled monolayers, respectively, representing embodiments of the invention.

FIG. 4 illustrates four self assembled monolayer chemical structures mapped across a two dimensional array, representing an embodiment of the invention.

FIG. 5 illustrates a group of four multi-chemical gradient areas, representing an embodiment of the invention.

FIGS. 6A and 6B illustrate structural diagrams of a field effect sensor and a capacitance/impedance sensor, respectively, representing embodiments of the invention.

Figure 9A:
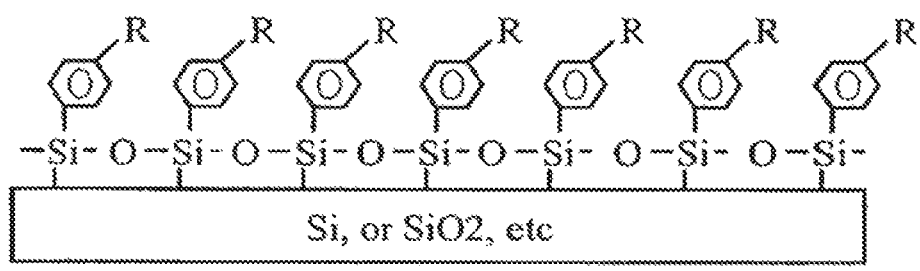
FIG. 9A illustrates a schematic representation of a substrate of silicon or glass modified with a self aligned monolayer of trichlorophenylsilane, representing an embodiment of the invention.
Figure 9B:
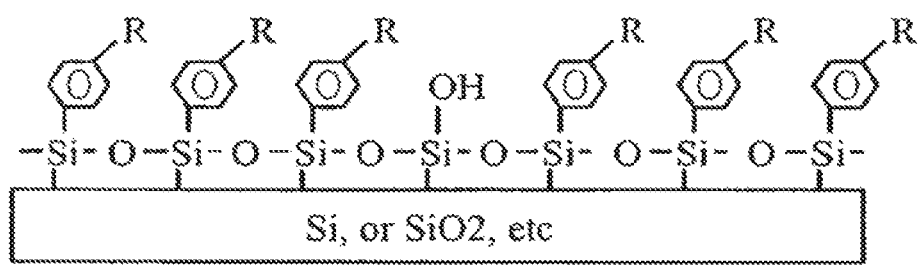
FIG. 9B illustrates a schematic representation of a first self aligned monolayer (SAM) of trichlorophenylsilane exposed to about 50 mJ of ultraviolet light at ~250 nm in clean room air. (~10% of dose to clear all phenyl groups), representing an embodiment of the invention.
Figure 9C:
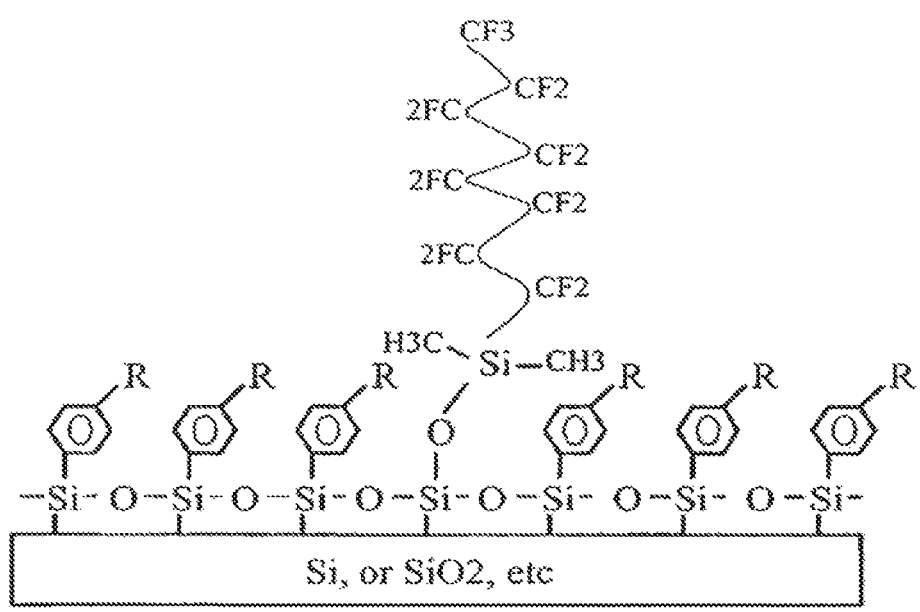
FIG. 9C illustrates a schematic representation of co-planar self aligned monolayers after initial exposure and formation of a second self aligned monolayer (SAM2), representing an embodiment of the invention.
Figure 9D:
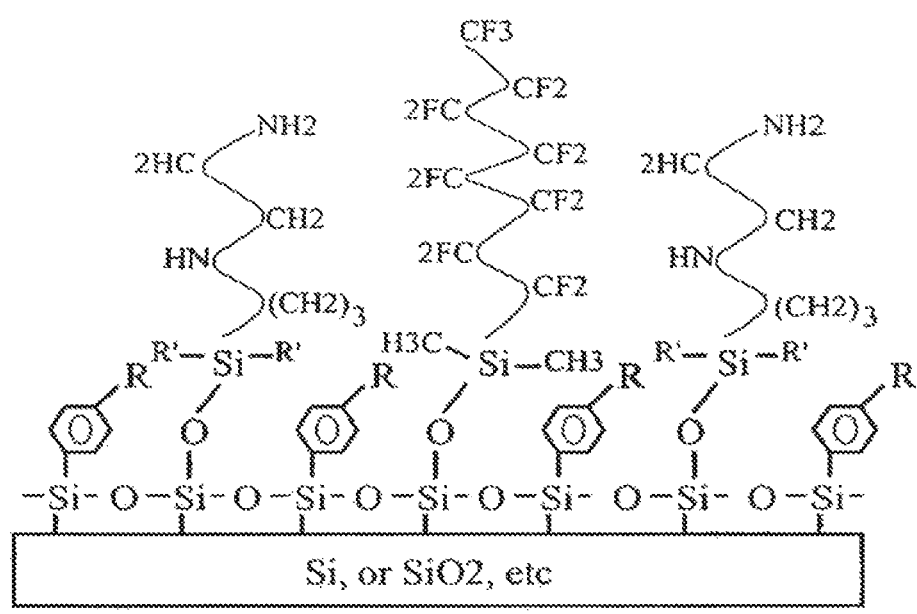

FIG. 9D illustrates a schematic representation of a final composition of SAM, SAM2, & SAM3 example after using 2 exposures of about 50 mJ (initial exposure) and 100 mJ (subsequent exposure) of ultraviolet light at ~250 nm, representing an embodiment of the invention.

Figure 10A:
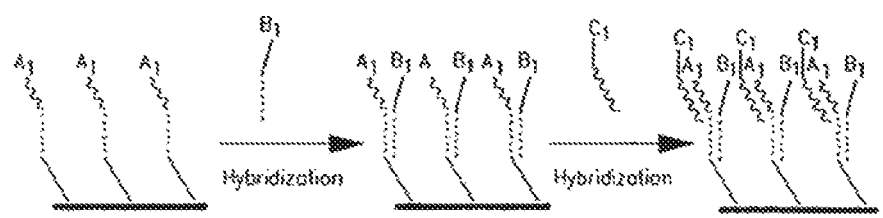
Figure 10B:
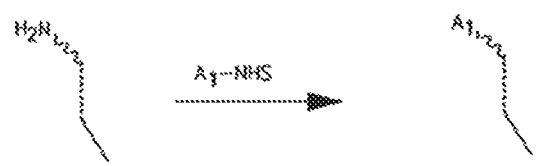

FIGS. 10A and 10B illustrate DNA-based self-assembly examples, representing embodiments of the invention.

Figure 11:
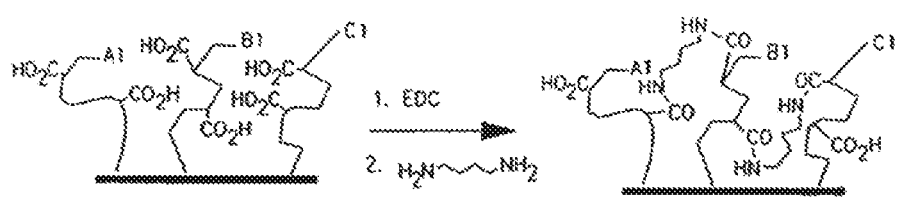

FIG. 11 illustrates a cross-linked polymer example, representing an embodiment of the invention.

Figure 12A:
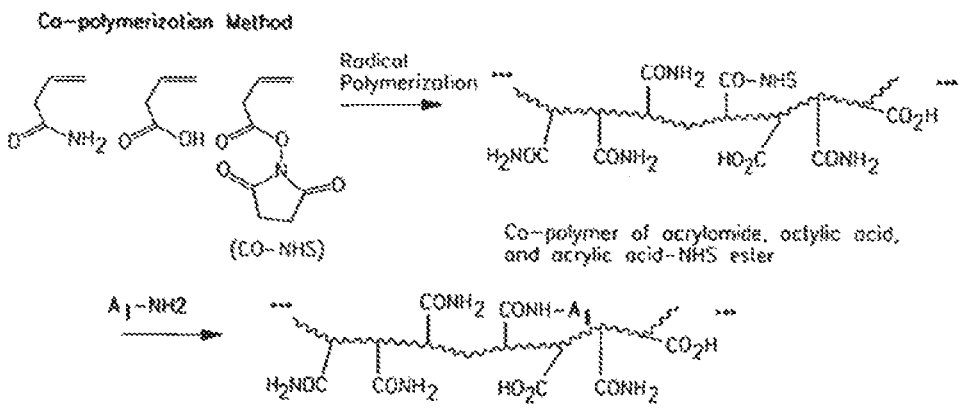
Figure 12B:
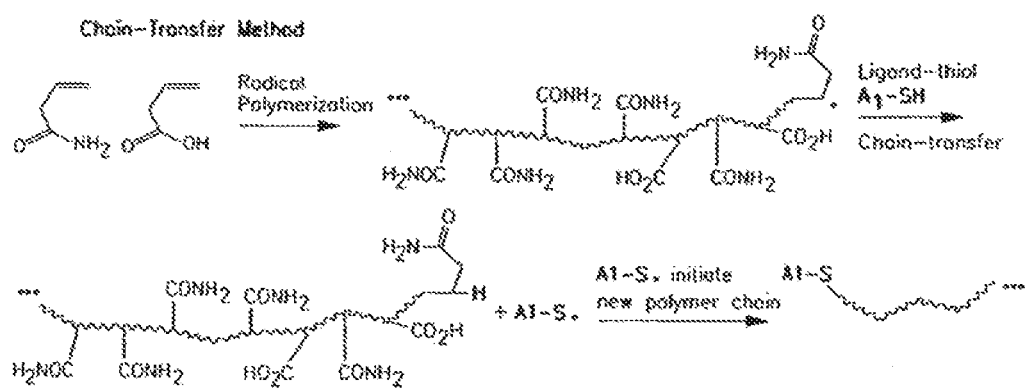
Figure 13A:
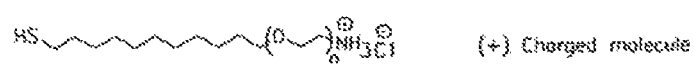
Figure 13B:
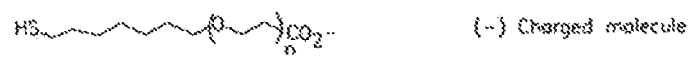
Figure 13C:
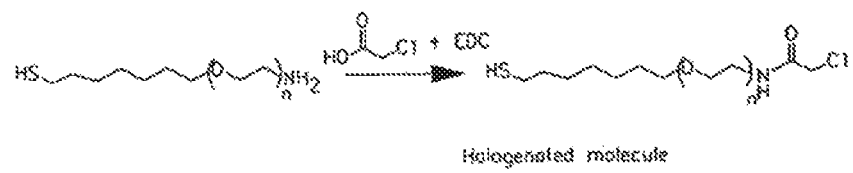
Figure 13D:
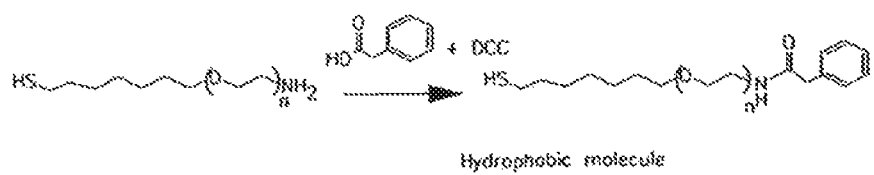

FIGS. 12A, and 12B illustrate co-polymerization and chain transfer examples, respectively, representing embodiments of the invention.

FIGS. 13A-13D illustrate thiol-PEG based examples, representing embodiments of the invention.

The embodiments of the invention and the various features and advantageous details thereof are explained more fully with reference to these non-limiting embodiments that are illustrated in the accompanying drawings and detailed in the following description. Descriptions of well known starting materials, processing techniques, components and equipment are omitted so as not to unnecessarily obscure the embodiments of the invention in detail. It should be understood, however, that the detailed description and the specific examples, while indicating preferred embodiments of the invention, are given by way of illustration only and not by way of limitation. Various substitutions, modifications, additions and/or rearrangements within the spirit and/or scope of the underlying inventive concept will become apparent to those skilled in the art from this disclosure.

The descriptions herein of the invention and preferred and alternative embodiments may be better understood in view of the following definitions:

The term "non-polymer" refers to polyatomic organic molecules that do not have repeated units that are either identical or non-identical.

The term "protein chip" refers to a two or three dimensional device that contains immobilized protein species (2 or more proteins) that are arranged in regular patterns or irregular patterns.

The term "optical sensing structure" refers to a device that collects photons from other objects and converts them to electrical signals.

The term "reaction cavity" refers to a 3D space that can hold reactants and allow chemical or biochemical reactions to proceed, typically measured in nanometer or micrometer scales.

The term "feature size" refers to the dimension(s) of an individual feature of a given array. For example, a protein array may have 100 protein spots. Thus the protein spots are the features of the protein array. The dimension of a given spot is the feature size of the spot. It can be measured by area, diameter or lengths of sides.

The phrase "coupling via thiol-based reaction product" refers to covalent bonding formation involving a hydrosulfide group (—SH). It can happen between organic compounds or between a thiol-containing organic compound and metals, such as gold and silver.

A substrate of an apparatus in accordance with a preferred embodiment includes an array of regions defining multiple cells. Each of the cells includes a reaction cavity that contains multiple functional binding groups. The substrate includes a solid material that provides support as well as a functional surface. The substrate can be made up of any of several materials, and preferably inorganic materials such as silicon wafer, glass, metal (aluminum, e.g.), or organic material such as plastic (polycarbonate, e.g.). The surface of the substrate is preferably coated with metal (gold) or a polymer (PEG) or both. Functional groups on the surface may include amine groups or carboxyl groups.

The multiple functional binding groups may be coupled to the substrate via hybridized DNA, a cross-linked polymer, a copolymer, a chain transfer polymer and/or a thiol-based reaction product. The cells preferably each include an analyte sensing structure such as an electrical sensing circuit or an optical sensing structure.

The cells may each comprise a protein chip or gene chip having a feature size preferably between 0.5 microns and 500 microns, and preferably less than approximately 100 microns. The cells may each comprise an electrically-active, combinatorial-chemical (EACC) chip for biochemical analyte detection. The analyte detection may be probe-less. The groups may include non-polymeric components.

The array may include a first density gradient of a first group in a first direction, and may further include a second density gradient of a second group in a second direction. The second direction may be approximately orthogonal to the first direction. Moreover, four significant directions may include, e.g., from an overhead viewpoint, left to right, right to left, up to down and down to up.

The substrate may comprise silicon having a surface modified with silanes, wherein the silanes may comprise phenyl. The multiple groups may include a positively-charged group and a negatively charged group and/or a polar group and a non-polar group.

A method of detecting an analyte uses a substrate including an array of regions defining multiple cells. Each of the cells includes a reaction cavity containing multiple functional binding groups. A channel may be defined between a source and a drain, although not necessarily, or a region may be defined between a pair of electrodes. A voltage is applied between the source and the drain or the pair of electrodes. A parameter indicative of an analyte characteristic is monitored when the voltage is applied. Each of the cells may include an analyte bonded to a self-assembled monolayer to define a channel or region between a source and drain or pair of electrodes, respectively.

A method of making an analyte sensor uses a substrate including an array of regions defining a plurality of cells each including a reaction cavity. Multiple functional binding groups are coupled to each reaction cavity. An analyte sensing structure is formed including the substrate with the array of regions. An analyte is preferably bonded to the multiple functional binding groups of each reaction cavity.

The forming of the analyte sensing structure may include forming a source and a drain for each reaction cavity such that each reaction cavity may define, although not necessarily, a channel between the source and the drain, and coupling a voltage source and monitoring system between the source and the drain, or it may include forming a pair of electrodes for each reaction cavity, and coupling a voltage source and monitoring system between the pair of electrodes. It may also include forming an optical sensing structure.

The method may include modifying a surface of the substrate with silanes, and the silanes may comprise phenyl. Modifications methods may include any of a variety of techniques such as adsorption or charge interaction.

A first gradient of a first group may be formed in a first direction of the array, and a second gradient of a second group may be formed in a second direction of the array. The first and second directions may be orthogonal. Third and fourth directions would include those opposite to the first and second directions.

An apparatus in accordance with an embodiment of the invention includes a substrate that includes an array of regions defining multiple cells, wherein each of the cells includes a reaction cavity that contains multiple functional binding groups. Another embodiment involves a method of detecting an analyte comprising providing a substrate including an array of regions defining multiple cells. Each of the cells includes a reaction cavity containing multiple functional binding groups and defining a channel between a source and a drain or defining a region between a pair of electrodes. In a method in accordance with this embodiment, a voltage is applied between the source and the drain or the pair of electrodes, and a parameter indicative of an analyte characteristic is monitored when the voltage is applied.

Another embodiment includes a process of fabricating an electrically active combinatorial-chemical chip for biochemical analyte detection comprising providing a substrate including an array of regions defining multiple cells each including a reaction cavity. Multiple functional binding groups are coupled to each reaction cavity. In a process in accordance with this embodiment, an analyte is bonded to the multiple functional binding groups of each reaction cavity, and an analyte sensing structure is formed including the substrate with the array of regions. Reaction cavities may be coupled with different functional binding groups or different molecules containing different groups.

To address the problems of creating a large number of specific probes, immobilizing them in small surface areas and applying the chips to samples containing unknown analytes, an embodiment of the invention can adopt a "probe-less" approach. An embodiment of the invention can vary surface properties to selectively attract proteins and/or other molecules. An embodiment of the invention can include creating a binding site with several small molecules (binding components). Small molecules and/or binding components are intended to mean non-polymeric molecules (e.g., can be hetero-oligomers). To achieve this, a limited number of binding components. (e.g., groups or molecules, covalently attached or adsorbed) can be used in different ratios and densities to obtain a large number of different chemical matrices that have different binding potentials to different analytes. Biochips made by this method can be termed combinatorial chemical (CC) chips.

An embodiment of the invention can use multiple small compounds (binding components) to assemble arrays of combinatorial chemical matrices for specific analyte binding and detections. Detections can be achieved optically, electronically or electrically. Thus, an embodiment of the invention can eliminate costly and time-consuming specific probe generation and also allow detection of not-yet-identified analytes. An embodiment of the invention is useful for sample profiling, and it is particularly useful for the analyses of proteins as well as other bio-analytes.

Referring to FIG. 1C, a basic element of an AECC chip embodiment of the invention is depicted. A substrate 170 can provide structural support. A first binding group 181 is coupled to the substrate 170. A second binding group 182 is also coupled to the substrate 170 at an inter-molecular distance from the first binding group 171. An analyte 190 binds to both the first binding group 181 and the second binding group 182. The inter-molecular distance between the first binding group 181 and the second binding group 182 corresponds to the inter-molecular distance between the binding locations on the analyte 190. This embodiment of the invention is based on the principle of using different molecules (binding groups) for specific binding of analytes. This embodiment of the invention is very flexible, very compact, sensitive, fast, reasonably specific and accurate. The identification of the analyte depends on the binding pattern of the analyte in the reaction cavities of the apparatus and prior information derived from known analytes.

An embodiment of the invention can include: a chip surface divided into multiple sub-areas (regions), each said sub-area can be coated with a combination of different binding components, said binding components can be organic compounds; said different binding components can vary in size, composition, and arrangement of functional groups; the ratios and densities of said binding components can be different among different sub-areas and these sub-areas can be identifiable (indexed) by X-Y coordinators.

In an embodiment of the invention, binding of an analyte on a sub-area can require the presence of 2 or more binding components. An electrical potential can be applied individually to or sensed individually from each sub-area; analyte binding can be detected electrically or electronically; and these detection methods can be used for analyzing (profiling) of biological or chemical samples.

An embodiment of the invention can include a chip having a planar surface with an array of sub-areas; each of the sub-areas can have 1 or more micro or nano-wells (i.e., reaction cavities). Under each such sub-area or well, there can be an electronic sensor and/or electrical structures(s) (e.g., transistors or electrodes for electrical detections). Different chemicals (for instance, 2, 3, 4 or more) cart be applied on the surface. When used in different ratios and different densities, a large number of combinations of chemicals (permutations) can be created. A simple way to generate different ratios is to create different gradients from the binding compounds, each of the gradients corresponding to one of the binding components.

Referring to FIG. 2, a multi-chemical-gradients (MCG) chip 200 embodiment of the invention is depicted. The top portion of the figure depicts a top plan view and the bottom portion of the figure depicts a partial cross section view. In this embodiment, A, B, C and D are 4 different chemical compounds. As depicted, A-B gradient(s) vary from between right and left and are represented by the horizontal double ended arrow. As depicted, C-D gradient(s) vary from between top and bottom and are represented by the vertical double ended arrow. In this embodiment, a surface 210 of a substrate 220 of the chip 200 includes an array of regions, each of which defines a sub-area 230. Each of the sub-areas 230 includes a sensor unit 240 which in-turn includes a nano-well 250 (reaction cavity) and a semiconductor or electrical sensor 260.

Referring to FIGS. 3A-3C, the chemicals (e.g., compounds of the binding components and solvents/vehicles) can be delivered to the surface of the wells by printing methods. Referring to FIG. 3A, a printing head 310 is coupled to a pair of mixers 320 each of which is in-turn coupled to a pair of reservoirs 330. The printing head 310 can deliver a predetermined ratio of A/B/C/D to a substrate surface 340. Referring to FIG. 3B, a plurality of filled binding cavities 350 is arranged above a plurality of sensors 360 on the substrate. Referring to FIG. 3C, preferably, self-assembled mono-layers (SAM) 370 are formed in each well (reaction cavity 350). For example, the bottom of the well can be coated with gold, a thiol-polyethylene glycol (PEG) derived compound can be used as a base component and compounds with similar (or the same) base structure(s) together with additional functional groups on the other end of the similar base structure molecules are the binding components and used together with base component to form a mixed SAM (self assembled monolayer). The functional groups associated with the binding components play the binding roles in analyte binding.

Referring to FIG. 4, four schematic examples of combinatorial chemical structures are depicted. The organic compounds used as binding components have different functional groups. Positively charged (PC) compounds are typically compounds with amino groups. Negatively charged (NC) compounds can be those containing carboxyl groups, sulfate group and phosphate groups. Compounds which are hydrophobic (nonpolar (NP)) can be those with benzyl ring structures and alkyl chains. Other compounds that are hydrophilic (polar (p)) can also be used, such as compounds with hydroxyl group, amine group, or organic compounds with hetero-atoms (e.g., nitrogen, oxygen). Organic compounds with halogen atoms can also be used. Compounds with reactive compounds groups may also be used, such as compounds with a thiol group, or an aldehyde group. Short peptides, including non-natural amino acids and oligo nucleotides (including those with modified structures) can be used together with other organic compounds. Other factors can also be considered in fabricating CC chips: for example, molecular chain length, position of functional groups, distance between functional groups, number of functional groups per molecule, ratio of mixed functional groups per molecule, arrangement of mixed functional groups on a molecule. These factors are important in generating 3-dimensional binding sites.

Referring to FIG. 5, CC chip can also be made with more than 4 chemical conditions (independent variables). For instance, the binding components (functional groups can be structurally arranged in a molecule to provide a contextual condition. In this way, an additional condition can be molecular chain length. The position of functional groups in a molecule can be another condition. The distance between function groups can be a condition. The number of functional groups per molecule can be a condition, the ratio of mixed functional groups per molecule can be a condition. The arrangement of mixed functional groups in a molecule can also be a condition. Also, the total density of functional groups on surface (region) can be a condition.

Referring to FIGS. 6A-6B, 7 and 8A-8C, different electrical/electronic sensors can be used together with a CC chip. Optical sensors can also be used together with a CC chip. In the case of an active electrical/electronic sensor, the chip can be termed an electrically active CC chip or EACC chip. For example, field-effect-transistor sensors, capacitance and impedance sensors and/or static-electric sensors can be integrated in the chip. Ideally, there is a sensor associated with each reaction cavity and each of the sensors is controlled independently.

Referring to FIG. 6A, a field effect measurement embodiment is depicted. An analyte 610 in a reaction cavity 620 with aqueous buffer is bonded to an SAM layer 630 to define a channel 640 on a substrate 650. The channel 640 is located between a source 645 and a drain 655 which are both coupled to a voltage source and monitoring system 660. Referring to FIG. 6B, a capacitance or impedance measurement embodiment is depicted. The analyte 610 is again bonded to the SAM layer 630 to define the channel 640 on the substrate 650. In this embodiment, the channel 640 is located between a first electrode 670 and a second electrode 675 which are both coupled to a voltage source and monitoring system 660.

Figure 7:
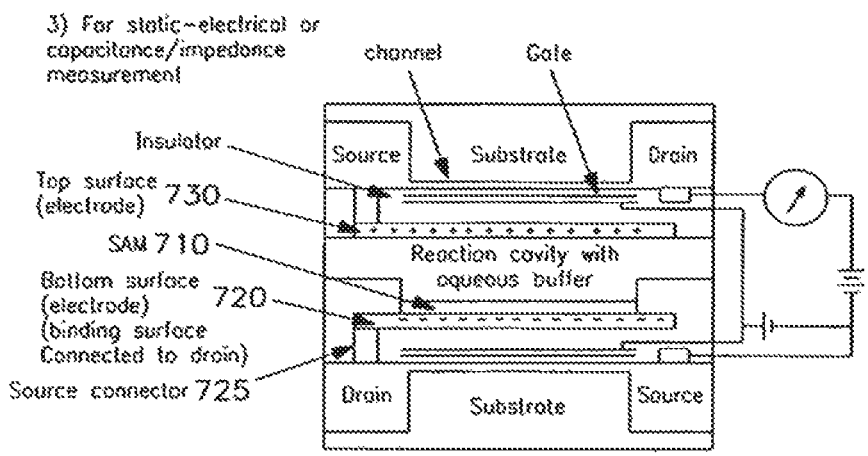
FIG. 7 illustrates a structural diagram of a sensor for static-electrical or capacitance/impedance measurements, representing an embodiment of the invention.

Referring to FIG. 7, a co-planar electrode static-electrical or capacitance/impedance measurement embodiment is depicted. A self aligned monolayer 710 is connected to a bottom surface electrode 720. The bottom surface electrode 720 is coupled to a source connector 725. A top surface electrode 730 is located opposite the self aligned monolayer 710 across a reaction cavity with aqueous buffer.

Sample binding: any biochemical or chemical samples can be used, provided chips with affinity surfaces are used. Conditions for sample binding and washing can be similar to those used in standard chromatography procedures: ion exchange, size exclusion, affinity binding, reverse phase binding (e.g., varying pH, ionic strength, solvent concentration) Sample concentrations, binding time and washing conditions can also be modified from the standard procedures. A microfluidic system (or micro electromechanical system (MEMS)) can be combined with the chip.

Figures 8A, 8B, 8C:
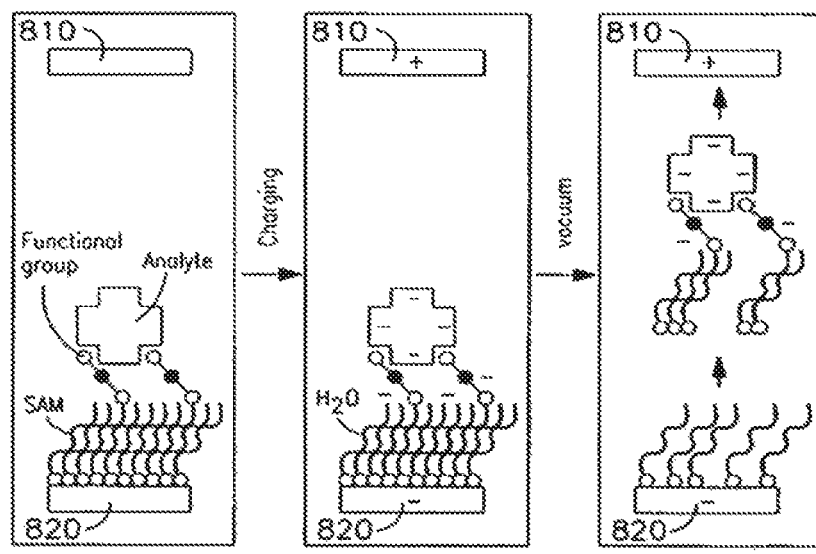
FIGS. 8A-8C illustrate static-electrical detection of an analyte, representing an embodiment of the invention.

Detection: Field effect, capacitance and impedance can be monitored for each reaction cavity, provided suitable electrical/electronic structures are made in the chip. An external chip reader is preferably used to collect and analyze the data. FIGS. 8A-8C illustrate an example of detection based on static-electric attraction. After selective binding and washing, an electrical potential is applied between a top surface of the chip 810 and a bottom surface of the chip 820. After drying by vacuum, electrical charges are built up around the molecules. The charges make the molecules move (fly) toward the top surface. Because the top plate can have a transistor (charge detector) corresponding to those in the bottom plate, molecular charging and flying can be regulated and detected independent of those in other reaction cavities.

Several transistors can be in a cell (reaction cavity) with the gates of the transistors coupled to the binding molecules. An SAM layer may not be necessary due to the importance of the distance between the analytes and the gate surface (i.e., the closer the better). The binding of the analytes close to the gate can affect electron distribution and thus the conductance of the transistor (between source and drain). Another type of structure in a cell (cavity) is a combination of electronic sensor (transistor) and electrical sensor (electrode for impedance measurement).

Data interpretation can be based on the premise that no specific probes or binding partners are required. Therefore, data obtained should be compared to reference or control samples or to normalized data. Algorithms can be trained and used to address particular problems.

Embodiments of the invention are applicable to clinical, research, pharmaceutical, agriculture, and environmental protection. Samples may need fractionation or enrichment before contacting a chip. Different chips can be used for the same sample to get complete information of interest.

The invention can include modifying the surface of glass or silicon with silanes that contain phenyl or other aromatic moieties that have absorption at about 260 nm and below. These materials can form a self assembling monolayer (SAM) using standard microelectronics processing techniques such as those used to promote adhesion of photoresists in standard high volume manufacturing (HVM) processing.

Referring to FIG. 9A, an embodiment of the invention is depicted as including a self aligned monolayer (SAM) on a substrate of silicon, silica, or metal oxides. In the case of simple aromatic groups R can be, e.g., hydrogen, amine, ethylenediamine, cyano, methyl, or fluorine groups. Therefore, the starting SAM can have many different chemical characteristics that determine the surface energy, polarity, and capability to attach additional moieties to or just be a relatively inert reaction well characterized starting surface for further modification using deep ultra violet (DUV) light. An embodiment of the invention can use a phenyl group (R=H) for the example depicted in FIGS. 9A-9D.

Once the substrate has been treated it can be exposed (flood or using high resolution mask) on a standard and readily commercially available DUV scanner or stepper. Because the Si—C bond is the weakest bond in the SAM what occurs is the breakage of that bond and the phenyl group is volatilized. In ambient atmosphere, the Si—: radical reacts with O2 & H2O to form SiOH. It is important to note that this is the same surface as the initial substrate surface, but before the formation of the SAM, and it is now one Si atom taller. The dose in mJ/cm2 to completely remove all of the phenyl groups is well documented in several publications and is on the order of 200 to 1000 mJ/cm2 and is also dependent on the type of aromatic and organic group chosen for the original SAM. For instance, it can be assumed that 500 mJ/cm2 is the dose to remove all the phenyl groups.

Referring to FIG. 9B, the resulting surface after the substrate and SAM has been exposed to 50 mJ/cm2 is depicted. After exposure ~10% of the surface is now available for a 2nd SAM to be formed. It is most important to note in this example that 2nd SAM material may have no aromatic group and, therefore, will not be affected by subsequent DUV exposures because it has substantially no absorption in the DUV spectrum, i.e., above ~200 nm. In this example, perflourooctyldimethylchlorosilane is used (SAM2) as the next SAM formation material. Treatment of the exposed surface with SAM2 will yield a new surface containing ~10% of SAM2 and 90% of the original phenyl silane SAM as depicted in FIG. 9C.

In this example, one additional exposure/SAM formation using a trimethoxysilane N-(2-aminoethyl-3-aminopropyl) trimethoxysilane SAM3 is performed, but this process could be continued to build a very large variety of well defined surfaces. In this example a 2nd exposure is 100 mJ and will remove ~20% of the remaining phenyl groups and following treatment with SAM3 will create a surface with ~20% SAM3 ~10% SAM2 and ~70% of the original SAM as depicted in FIG. 9D.

This procedure could be continued to put more SAMs of known concentration on the surface and subsequent surface chemistry can be done to attach bio-relevant chemistry such as antibodies, DNA, or RNA, to the appropriate R group on the SAM. The surface can thus be patterned in arrays very easily and even have high resolution (<100 nm line/space) within an array. This embodiment of the invention makes it feasible to make arrays of well defined surface chemistry with minimal reticles or masks.

For instance, if it were desired to make small areas (100 um square) of well defined, but different surface concentrations of the three SAMs described above on bare Si metal oxides or glass, the following technique could be used. The surface can be treated with photosensitive trichlorophenylsilane and then exposed via a 10 um×10 um array with dose increments of 5 mJ/cm2 (i.e., ~1% the does assumed above to be required to remove all the phenyl groups) over a range from 0-500 mJ/cm2. Then SAM2 formation can be performed resulting in 10×10 array containing a ratio of the $1^{st}$ two SAMs of from approximately 0% to approximately 100% across the array. The $2^{nd}$ exposure can then be performed but in reverse spatial arrangement of the increments, or with any desired dose range, to yield many different surfaces of known composition. Specifically, with a reverse exposure starting at 500 mJ and going to 0 in the same increments, the result would be 10×10 array that contains ~100% SAM2 & SAM3, but with ~0% of the original SAM.

However, in another instance, an embodiment of the invention could utilize the same range and not reverse dose, and this would result in an array with ~100% original SAM and with the SAM2 & SAM3 ncreasing in concentration by 1% each until they reach ~50% each of the surface concentration half way through the array. From then on SAM2 would continue to increase by 1% and SAM3 would decrease by 1% with ~0% of original same making up the concentration of the surface until 100% SAM2 is reached at last exposure field. The variations on this sub-generic scenario are enormous. The same examples described above can work with 193 nm exposure which will make the aromatic photosensitive SAMs more efficient but will also make many of the non-aromatic SAMs slightly sensitive to each of the subsequent exposures, but since they are so much less absorbing they will be much less involved in the photochemical cleavage, and therefore they are just accounted for in determining the final composition of the surface.

While not being limited to any particular performance indicator or diagnostic identifier, preferred embodiments of the sensor array can be identified one at a time by testing for the presence of sensing with respect to a known concentration of target analyte. The test for the presence of sensing can be carried out without undue experimentation by the use of a simple and conventional impedance spectroscopy experiment. Among the other ways in which to seek embodiments having the attribute of sensing guidance toward the next preferred embodiment can be based on the presence of a characteristic IR spectroscopy signal.

Embodiments of the electrically active combinatorial-chemical chip for biochemical analyte detection can be identified by scanning electron microscope (SEM) cross-sections. Embodiments of the electrically active combinatorial-chemical chip for biochemical analyte detection can also be identified by material analysis of devices containing sensors using techniques such as Auger spectroscopy and/or dynamic secondary ion mass spectroscopy.

Embodiments of the invention can include impedance spectroscopy, amperommetry, voltammetry and other electrochemical techniques used to generate a response from adsorbed analyte through the electrodes/probes. Embodiments of the invention can include the use of optical techniques such as FTIR spectroscopy can be used to identify the functional groups of analyzed chemicals species.

Specific embodiments of the invention will now be further described by the following, nonlimiting examples which will serve to illustrate in some detail various features. The following examples are included to facilitate an understanding of ways in which embodiments of the invention may be practiced. It should be appreciated that the examples which follow represent embodiments discovered to function well in the practice of embodiments of the invention; and thus can be considered to constitute preferred modes for the practice of embodiments of the invention. However, it should be appreciated that many changes can be made in the exemplary embodiments which are disclosed while still obtaining like or similar result without departing from the spirit and scope of embodiments of the invention. Accordingly, the examples should not be construed as limiting the scope of embodiments of the invention.

EXAMPLES

Example 1

Referring to FIGS. 10A and 10B, a DNA-based self-assembly structure is provided for affinity binding array. A single-stranded oligonucleotide with one or more "coding regions" and a binding ligand A1 is immobilized on one of the spots on an array surface (FIG. 10A). The binding ligands preferably include small molecules such as biotin, pyridine, furan, imidazole, pyran, benzene, purine, pyrimidine, benzoic acid, aniline, styrene, phenol, typtophan, or another compound of interest or as may be understood by those skilled in the art. The oligo nucleotide is from approximately 20 to approximately 100 bases long, and each coding region contains from approximately 10 to approximately 20 DNA bases with specific sequences; while the binding ligands are small molecules such as biotin, pyridine, furan, imidazole, pyran, benzene, purine, pyrimidine, benzoic acid, aniline, styrene, phenol, typtophan, or any other compounds of interest. The ligand can be attached to the oligonucleotide through known chemistry, e.g., N-hydroxysuccinimide ester (NHS) mediated conjugation (FIG. 10B), 1-Ethyl-3-(3-dimethyllaminopropyl)carbodiimide (EDC) catalyzed amide formation or reductive amination.

In general, there are several ways to immobilize DNA. A first would be charge attraction on a positively charged surface such as a surface coated with polysilane. A second would be covalent attachment through a molecular end such as a thiol attachment reaction with a metal. An amine group on DNA will react with a carboxyl group on a surface. A third way involves specific binding. For example, biotin on DNA may be captured by streptavidin on the surface.

After the immobilization, a second single-stranded oligonucleotide with one or more "coding regions" and ligand B1 was contacted with the substrate. The oligo nucleotide can be 20-100 bases long, and each coding regions can contains 10-20 DNA bases with specific sequences One of the coding regions of the second oligonucleotide should be complimentary to one of the coding region. Under hybridization condition (for example, incubation at 37° C. for 1 hour in 2×SSC buffer: 0.03 M sodium citrate, 0.3 M NaCl, pH approx. 7.0,) the two oligo nucleotide's will hybridize and thus the two ligands A1 and B1 will be localized.

Additional steps can be performed to add more ligand-oligonucleotides to the surface, resulted in a collection of ligands A1, B1, C1 . . . localized in the said array spot at certain orientation. On other array spots, different ligands or different combination of ligands can be applied to create another unique collection of ligands. Thus, an affinity array based on DNA self-assembly can be generated.

Solvents that can be used in the ligand incorporation step and the spotting step include water, salt buffer solution such as SSC, and organic solvent in which oligonucleotide is soluble, such as methanol and DMF (dimethyl Formamide). For the hybridization step, buffer solutions such as SSC, citrate, borate and phosphate with up to 50% of Formamide or urea can be used. The same format can be used to make PNA and RNA self-assembly arrays as well.

Example 2

Referring to FIG. 11, an embodiment of the invention includes a cross-linked polymer based structure for affinity binding array. Small molecule ligand A1 was incorporated into a cross-linkable polymers such as poly(acrylamide)-co-poly(acrylic acid), and other ligand B1, C1, was incorporated into other cross-linkable polymers individually. The cross-linkable polymer was selected from synthetic polymers such as polyacrylamide, polyacrylic acid, polyallyamine, polyvinylalcohol, and natural polymers such as polysaccharide and DNA.

Referring to FIGS. 12A and 12B, two possible incorporation methods are co-polymerization (FIG. 12A) and chain-transfer (FIG. 12B). In the co-polymerization method, a reactive monomer was added to the polymerization mix and the resulted co-polymer was reacted with ligand A1, B1, through the reactive function group NHS-ester. In the chain transfer method, the ligands were linked to a chain-transfer reagent such as thiol, and hence incorporated at the end of the polymer chain. Other polymer functionalization methods such as post-polymerization reaction can also be used.

A mixture of the ligand-loaded cross-linkable polymer was deposited on an array spot, and a cross-linker such as 1,4-diaminobutane was introduced after the polymers were activated by EDC (1-Ethyl-3-(3-dimethyllaminopropyl)carbodiimide). The resulting cross-linked polymer had the attached ligands (A1, B1, C1, . . . ) localized in the array spot. Using this method, each array spot was deposited with a different set of ligands, and an affinity array was built.

Preferred and alternative solvents that were and/or could be used in the ligand incorporation step, the spotting step, and cross-linking steps include water-based solvents such as water and buffer solutions such as citrate, borate and phosphate; and organic solvent such as DMF (dimethyl Formamide), ethyl alcohol, methanol, iso-propanol, and THF (tetrahydrofuran). Other cross-linking methods such as glutaraldehyde crosslinking of amines or photo-initiated radical crosslinking of poly-acrylamide can also be used.

Example 3

Referring to FIGS. 13A-13D, an embodiment of the invention includes making combinatory chemical structures. PEG-based thiol compounds with combinatory chemical structures were made from thiol-PEG-amine or thiol-PEG-carboxylate. DCC=N,N'-dicyclohexylcarbodiimide. The molecular weight of these thiol-PEG chemical structures was from 200 to 5000, with 3-100 repetitive PEG units. The above reactions were performed in water, water-based buffer solution such as sodium phosphate solution, and organic solvents such as DMF and THF.

Generally, PEG polymers may be advantageously used, as in example 3, primarily to fill the surface spaces or gaps on a chip. It can reduce non-specific binding. If one end of the PEG polymers have thiol groups that can be attached to a gold surface, the PEG molecules can self-assemble into a monolayer on the gold surface. If a portion of the PEG polymers have functional groups (for example, examine groups), then the chip surface will be functionalized by the amine groups whose density is determined as a % of the amine-containing PEG polymers.

A practical application of embodiments of the invention that has value within the technological arts is integrating chemical and/or biological sensing with computing and communication. There are virtually innumerable uses for embodiments of this invention.

Embodiments of the invention are cost effective and advantageous for at least the following reasons. An embodiment of the invention obviates the need for specific probe synthesis as well as site-specific immobilization and only a limited number of small chemicals can be used in different combinations. An embodiment of the invention can have the advantage of simplifying chip fabrication. An embodiment of the invention can have a compact size and high capacity. Electrical detection allows fabrication of chips with very high sub-area density (protein chip with feature size <1 um), no optical system and thus chip reader can be very compact. An embodiment of the invention can be flexible and applicable to samples of different compositions and from different sources. An embodiment of the invention can have the advantage of detecting not-yet-identified analytes in that unknown compounds can bind to the EACC chips and be detected. In general, embodiments of the invention improve quality and/or reduce costs compared to previous approaches.

The terms "a" or "an", as used herein, are defined as including one and more than one. The term plurality, as used herein, is defined as including two and more than two. The term another, as used herein, is defined as at least a second or more. The terms "comprising" (comprises, comprised), "including" (includes, included) and/or "having" (has, had), as used herein, are defined as open language (e.g., requiring what is thereafter recited, but open for the inclusion of unspecified procedure(s), structure(s) and/or ingredient(s) even in major amounts. The terms "consisting" (consists, consisted) and/or "composing" (composes, composed), as used herein, close the recited method, apparatus or composition to the inclusion of procedures, structure(s) and/or ingredient(s) other than those recited except for ancillaries, adjuncts and/or impurities ordinarily associated therewith. The recital of the term "essentially" along with the terms "consisting" or "composing" renders the recited method, apparatus and/or composition open only for the inclusion of unspecified procedure(s), structure(s) and/or ingredient(s) which do not materially affect the basic novel characteristics of the composition. The term coupled, as used herein, is defined as connected, although not necessarily directly, and not necessarily mechanically. The term any, as used herein, is defined as all applicable members of a set or at least a subset of all applicable members of the set. The term approximately, as used herein, is defined as at least close to a given value (e.g., preferably within 10% of, more preferably within 1% of, and most preferably within 0.1% of). The term substantially, as usedherein, is defined as largely but not necessarily wholly that which is specified. The term generally, as used herein, is defined as at least approaching a given state. The term deploying, as used herein, is defined as designing, building, shipping, installing and/or operating. The term means, as used herein, is defined as hardware, firmware and/or software for achieving a result. The term program or phrase computer program, as used herein, is defined as a sequence of instructions designed for execution on a computer system. A program, or computer program, may include a subroutine, a function, a procedure, an object method, an object implementation, an executable application, an applet, a servlet, a source code, an object code, a shared library/dynamic load library and/or other sequence of instructions designed for execution on a computer or computer system.

All the disclosed embodiments of the invention disclosed herein can be made and used without undue experimentation in light of the disclosure. Embodiments of the invention are not limited by theoretical statements recited herein. Although the best mode of carrying out embodiments of the invention contemplated by the inventor(s) is disclosed, practice of the embodiments of the invention is not limited thereto. Accordingly, it will be appreciated by those skilled in the art that the embodiments of the invention may be practiced otherwise than as specifically described herein.

It will be manifest that various substitutions, modifications, additions and/or rearrangements of the features of the embodiments of the invention may be made without deviating from the spirit and/or scope of the underlying inventive concept. It is deemed that the spirit and/or scope of the underlying inventive concept as defined by the appended claims and their equivalents cover all such substitutions, modifications, additions and/or rearrangements.

All the disclosed elements and features of each disclosed embodiment can be combined with, or substituted for, the disclosed elements and features of every other disclosed embodiment except where such elements or features are mutually exclusive. Variation may be made in the steps or in the sequence of steps defining methods described herein.

Although the sensor array described herein can be a separate module, it will be manifest that the sensor array(s) may be integrated into the system with which it is (they are) associated. Similarly, although the hand held device described herein can be a separate module, it will be manifest that the hand held device(s) may be integrated into the system with which it is (they are) associated.

The sensor array may comprise an array of transistor sensors. Different chemical structures (groups or molecules) may be disposed on the gates of the transistors. A sample preferably contacts each of the gate-associated chemical structures. A set of pre-determined chemical structures are associated with a set of transistors. Different analytes interact with the pre-determined chemical structures differently, such that the patterns are unique. Binding patterns are translated into electrical signals by the transistors. The analytes in the sample may be identified by the pattern of electrical signals of the transistors with respect to the gate-associated chemical compositions. A database is preferably pre-built using standard analytes, and computer pattern recognition is used in the identification.

The individual components need not be formed in the disclosed shapes, or combined in the disclosed configurations, but could be provided in all shapes, and/or combined in all configurations. The individual components need not be fabricated from the disclosed materials, but could be fabricated from all suitable materials. Homologous replacements may be substituted for the substances described herein. Agents that are both chemically and physiologically related may be substituted for the agents described herein where the same or similar results would be achieved.

While an exemplary drawings and specific embodiments of the present invention have been described and illustrated, it is to be understood that that the scope of the present invention is not to be limited to the particular embodiments discussed. Thus, the embodiments shall be regarded as illustrative rather than restrictive, and it should be understood that variations may be made in those embodiments by workers skilled in the arts without departing from the scope of the present invention as set forth in the appended claims and structural and functional equivalents thereof.

In methods that may be performed according to the invention and/or preferred embodiments herein and that may have been described above and/or claimed below, the operations have been described in selected typographical sequences. However, the sequences have been selected and so ordered for typographical convenience and are not intended to imply any particular order for performing the operations.

The appended claims are not to be interpreted as including means-plus-function limitations, unless such a limitation is explicitly recited in a given claim using the phrase(s) "means for" and/or "step for." Subgeneric embodiments of the invention are delineated by the appended independent claims and their equivalents. Specific embodiments of the invention are differentiated by the appended dependent claims and their equivalents.

What is claimed is:

1. An apparatus, comprising a substrate including an array of regions defining a plurality of cells, each of the plurality of cells including a reaction cavity containing multiple functional binding groups, wherein the array of regions comprises a first gradient of a first functional binding group and a second gradient of a second functional binding group, wherein an inter-molecular distance between the first functional binding group and the second functional binding group corresponds to a distance between binding locations on a biochemical analyte, wherein the plurality of cells comprise a chip for analyte detection having a feature size between 0.5 microns and 500 microns and analyte detection comprises creation of a binding site with one or more of the multiple functional binding groups, wherein the substrate comprises trichlorophenylsilane.

2. The apparatus of claim 1, wherein the multiple functional binding groups are coupled to the substrate via hybridized DNA.

3. The apparatus of claim 1, wherein the plurality of cells each comprise an electrical sensing circuit.

4. The apparatus of claim 1, wherein the plurality of cells comprise a protein chip having a feature size between 0.5 microns and 500 microns.

5. The apparatus of claim 1, wherein the plurality of cells comprise a protein chip having a feature size of less than 100 microns.

6. The apparatus of claim 1, wherein the plurality of cells comprise a protein chip having a feature size of less than one micron.

7. The apparatus of claim 1, wherein the plurality of cells each comprise an electrically-active, combinatorial-chemical (EACC) chip for biochemical analyte detection.

8. The apparatus of claim 7, wherein said analyte detection comprises probe-less detection.

9. The apparatus of claim 1, wherein the groups comprise non-polymeric components.

10. The apparatus of claim 1, wherein the first gradient is in a first direction or in the opposite direction or a combination thereof.

11. The apparatus of claim 10, wherein the second gradient is in a second direction or in the opposite direction or a combination thereof.

12. The apparatus of claim 11, wherein the second direction is orthogonal to the first direction.

13. The apparatus of claim 1, wherein the multiple groups comprise a positively-charged group and a negatively charged group.

14. The apparatus of claim 1, wherein the multiple groups comprise a polar group and a non-polar group.

15. The apparatus of claim 1, further comprising a sensor in the reaction cavity, the sensor comprising at least one transistor with a source, a drain, and a gate; wherein the multiple functional binding groups are on the gate of the transistor.

16. The apparatus of claim 15, wherein the cells are configured for monitoring a parameter indicative of an analyte characteristic when a voltage is applied between the sources and drains of the transistors.

17. The apparatus of claim 1, further comprising a channel defined by an analyte bonded to a self-assembled monolayer.

* * * * *

UNITED STATES PATENT AND TRADEMARK OFFICE
CERTIFICATE OF CORRECTION

PATENT NO. : 10,655,166 B2  
APPLICATION NO. : 15/727296  
DATED : May 19, 2020  
INVENTOR(S) : Su et al.

Page 1 of 1

It is certified that error appears in the above-identified patent and that said Letters Patent is hereby corrected as shown below:

On the Title Page

In "Related U.S. Application Data", in Column 1, Line 1, delete "(60)" and insert --(63)-- therefor Signed and Sealed this  
Eighth Day of December, 2020

Andrei Iancu  
*Director of the United States Patent and Trademark Office*